US 7,819,834 B2

(12) United States Patent
Paul (10) Patent No.: US 7,819,834 B2
(45) Date of Patent: Oct. 26, 2010

(54) SYSTEM AND METHOD OF AIR EMBOLISM DETECTION AND DIVERSION

(75) Inventor: Gregory L. Paul, Chelsea, MI (US)

(73) Assignee: Terumo Cardiovascular Systems Corp., Ann Arbor, MI (US)

(*) Notice: Subject to any disclaimer, the term of this patent is extended or adjusted under 35 U.S.C. 154(b) by 621 days.

(21) Appl. No.: 11/654,964

(22) Filed: Jan. 18, 2007

(65) Prior Publication Data

US 2007/0173753 A1 Jul. 26, 2007

Related U.S. Application Data

(60) Provisional application No. 60/761,526, filed on Jan. 24, 2006.

(51) Int. Cl.
*A61M 37/00* (2006.01)
*A61M 1/00* (2006.01)
(52) U.S. Cl. ............... 604/6.1; 604/4.01; 604/6.09; 604/6.14; 422/44; 422/45
(58) Field of Classification Search ............ 604/5.01, 604/6.09, 6.14, 6.15, 6.16; 422/45
See application file for complete search history.

(56) References Cited

U.S. PATENT DOCUMENTS 3,722,680 A * 3/1973 Smith ................ 210/96.2
6,267,926 B1 * 7/2001 Reed et al. ............ 422/48
6,395,014 B1    5/2002 Macoviak et al.
6,824,524 B1 * 11/2004 Favre ............... 604/6.16
6,843,099 B2    1/2005 Derek et al.
2002/0031442 A1 * 3/2002 Knott .................. 422/45
2002/0114731 A1 * 8/2002 Stringer et al. .......... 422/44
2002/0176798 A1 * 11/2002 Linker et al. ........... 422/45
2004/0217054 A1 * 11/2004 Olsen et al. ............ 210/645
2006/0089586 A1 * 4/2006 Kaus et al. ............ 604/4.01
2006/0167400 A1    7/2006 Ellingboe et al.
2006/0231098 A1 * 10/2006 Downie et al. ........ 128/204.22
2007/0160495 A1 * 7/2007 Schreyer ............... 422/45
2008/0221498 A1 * 9/2008 Ogihara et al. ......... 604/6.11

* cited by examiner

*Primary Examiner*—Leslie R Deak
*Assistant Examiner*—Adam Marcetich
(74) *Attorney, Agent, or Firm*—Gail Diane Tisack; Mark L. Mollon (57) ABSTRACT

A perfusion system for treating blood during a surgical procedure uses a flow control valve with first and second inlets and first and second outlets. A first intermediate line couples the first outlet to an air removal system. A second intermediate line couples blood from the air removal system to the second inlet. An arterial line carries treated blood from the second outlet back to the patient. The flow control valve has an open position and a recirculate position, wherein the first inlet is coupled to the first outlet when the flow control valve is in either the open position or the recirculate position. The second inlet is coupled to the second outlet and blocked from the first outlet in the open position. The second inlet is coupled to the first outlet and blocked from the second outlet in the recirculate position.

9 Claims, 8 Drawing Sheets

SYSTEM AND METHOD OF AIR EMBOLISM DETECTION AND DIVERSION

CROSS REFERENCE TO RELATED APPLICATIONS

This application claims priority to co-pending U.S. provisional application Ser. No. 60/761,526, filed Jan. 24, 2006.

STATEMENT REGARDING FEDERALLY SPONSORED RESEARCH

Not Applicable.

BACKGROUND OF THE INVENTION

The present invention relates to a blood perfusion system used during surgery such as cardiovascular surgery wherein air emboli present in the perfusion circuit is efficiently removed by an air removal device before returning the embolus-free blood back to circulation in the patient.

During cardiac bypass surgery, the heart is stopped in order to allow repair of defects, such as the replacement of defective heart valves, or the placement of bypass grafts. The patient's blood is redirected through an extracorporeal perfusion circuit typically including various items such as a venous cannula, PVC tubing, a reservoir, a pump, an oxygenator, an arterial filter, and an arterial cannula. During extraction of blood from the patient and/or at various stages of flow within the perfusion circuit, air emboli may form within the circulating blood. If these emboli are not removed from the circulating blood and are instead introduced back to the patient's bloodstream, there may be serious complications.

Air or other gaseous emboli can be removed (i.e., filtered) from blood that is flowing in a perfusion circuit by passing it through an air removal system. A screen or mesh filter can be employed for this purpose. Other examples of air removal devices that can be used include those shown in co-pending U.S. application Ser. No. 11/118,726, filed Apr. 29, 2005, entitled "Air Removal Device with Float Valve for Blood Perfusion System", co-pending U.S. application Ser. No. 11/136,047, filed May 24, 2005, entitled "Vortex-Flow Air Removal in a Blood Perfusion System", co-pending U.S. application Ser. No. 11/245,751, filed Oct. 7, 2005, entitled "Float-Driven Lever Arm for Blood Perfusion Air Removal Device", and co-pending U.S. application Ser. No. 11/245,752, filed Oct. 7, 2005, entitled "Blood Perfusion Air Removal Device with Arcuate Manifold", all of which are incorporated herein by reference in their entirety.

Some currently available perfusion systems monitor the fluid level in the perfusion circuit reservoir using a level sensor in order to infer that air emboli are present when the level in the reservoir is too low. It is known to display or sound an alert signal when the level in the reservoir drops below a predetermined threshold limit (or when emboli are otherwise detected, such as with an ultrasonic sensor). In response to the alarm, the circulation is manually stopped by a health care professional (such as a perfusionist) as quickly as manually possible. Special steps must then be taken to remove the air emboli before restoring the circulation back to the patient.

The perfusionist has many tasks to perform in the operating room during cardiac surgery and the corresponding distractions can lengthen the response time for stopping circulation when an alarm is triggered. Therefore, there is a need in the art for a means of automatically stopping the emboli before it reaches the patient without having to wait for action from the perfusionist.

Besides the need to quickly divert any emboli from reaching the patient, it is very important to clear the emboli from the blood in the perfusion circuit so that circulation to the patient can be restored as soon as possible. Once circulation is stopped in the perfusion circuit, it is time consuming for the perfusionist to isolate the quantity of blood containing the emboli and remove the emboli. Therefore, there is also a need in the art for a means of quickly purging emboli in order to safely restore blood circulation to the patient.

SUMMARY OF THE INVENTION

The present invention protects the patient from emboli in blood by automatically diverting emboli-containing blood away from the patient and then quickly removing the emboli by recirculating the blood through an air removal device. When the excess air has been removed from the blood, then circulation to the patient can be manually or automatically restored.

In one aspect of the invention, a perfusion system is provided for treating blood of a patient during a surgical procedure. A venous line carries blood removed from the patient. A flow control valve has first and second inlets and first and second outlets, wherein the venous line is coupled to the first inlet. An air removal system is provided for removing emboli from the blood flowing in the perfusion system. A first intermediate line couples the first outlet of the flow control valve to the air removal system. A second intermediate line couples blood having passed through the air removal system to the second inlet of the flow control valve. An arterial line couples to the second outlet of the flow control valve for carrying treated blood back to the patient. The flow control valve is selectably placed in an open position or a recirculate position, wherein the first inlet is coupled to the first outlet when the flow control valve is in either the open position or the recirculate position. The second inlet is coupled to the second outlet and blocked from the first outlet when the flow control valve is in the open position. The second inlet is coupled to the first outlet and blocked from the second outlet when the flow control valve is in the recirculate position.

DETAILED DESCRIPTION OF PREFERRED EMBODIMENTS

Figure 1:
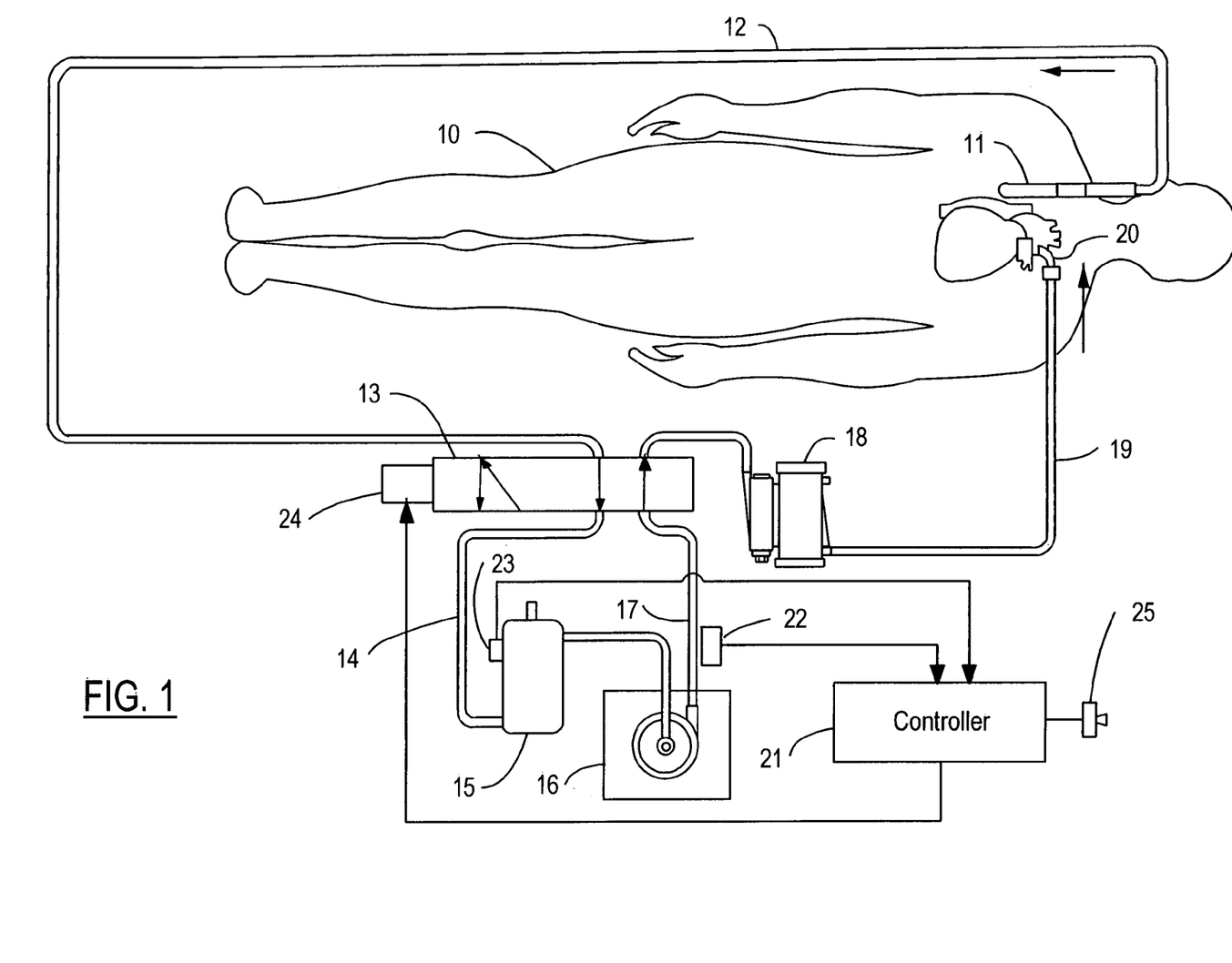
FIG. 1 is a schematic view of a perfusion system according to one embodiment of the present invention.

Referring now to FIG. 1, a perfusion system supporting a patient 10 includes a venous cannula 11 supplying the patient's blood to a venous line 12 is connected to an inlet of a flow control valve 13. An intermediate line 14 passes the blood flow to an air removal system 15 and then to a blood pump 16. Another intermediate line 17 provides blood flow from pump 16 to a second inlet of flow control valve 13.

In a normal operating mode, blood from pump 16 is passed from valve 13 through an oxygenator 18 to an arterial line 19 and to an arterial cannula 20 for return to the patient. Thus, flow control valve 13 is shown in an open position such that substantially all emboli are removed from the flowing blood by air removal system 15 and the blood is passed through oxygenator 18 back to the patient.

In order to detect and react to emboli that may be entrained in the blood, a controller 21 is used to detect the presence of excessive air emboli and to prevent emboli-containing blood from reaching the patient. Thus, controller 21 is connected to a gas sensor 22 and/or a level detector 23. Gas sensor 22 may comprise an ultrasonic detector disposed in contact with intermediate line 17 for measuring an overall volume of emboli present in predetermined volumes of blood, as is known in the art. Level sensor 23 is contained on or within air removal system 15. Air removal system 15 utilizes a reservoir of blood upon which it acts to remove gas bubbles. A condition wherein the volume of blood present in the reservoir is less than a predetermined volume of blood results in a reduction of the ability to remove emboli from the blood. In response to either type of sensor indicating that excessive emboli are present, controller 21 actuates a mechanical actuator 24 on flow control valve 13 to move it from the open position shown in FIG. 1 to a recirculation position which redirects blood from intermediate line 17 back to air removal system 15. Simultaneously, controller 21 supplies an alert signal to an annunciator 25 such as a loudspeaker or a visual display. Sensor 22 and 23 may be used alone or together depending upon the specific air removal system being used, for example.

Figure 2:
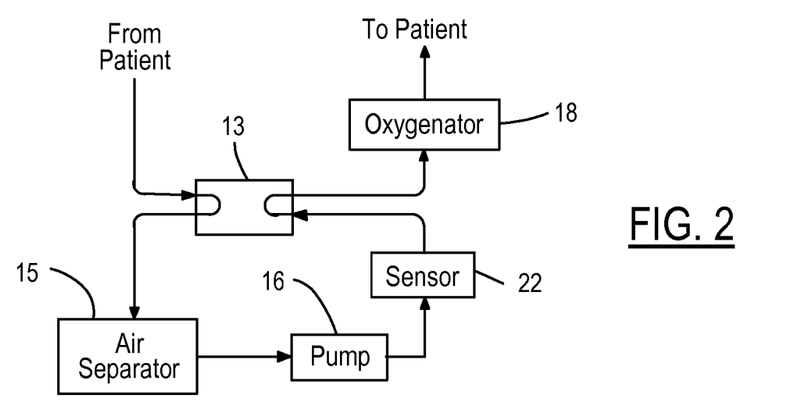
FIG. 2 is a diagram showing blood flow during a normal operating mode of the perfusion system.
Figure 3:
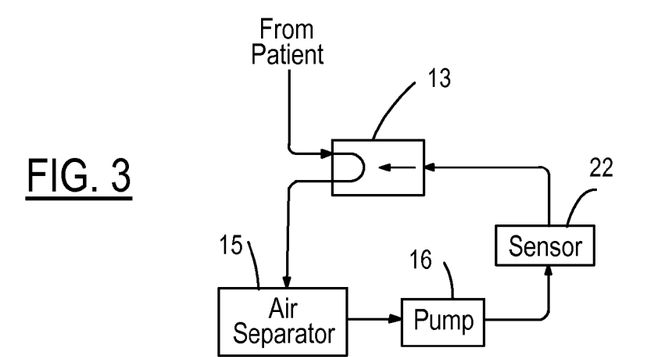
FIG. 3 is a diagram showing blood flow during a recirculating mode of the perfusion system.

FIG. 2 represents the normal operation mode with flow control valve 13 in the open position. Blood from the patient is drawn through valve 13 and air separator 15 by pump 16. The blood flows past sensor 22, through the second set of ports on valve 15, to oxygenator 18, and finally back to the patient. FIG. 3 shows the perfusion system in a recirculate mode with blood from the patient being drawn through valve 13 and through air separator 15 by pump 16. Blood pumped by pump 16 past sensor 22 containing excessive emboli is coupled by valve 13 back to the flow going to air separator 15. Importantly, both the recirculated blood from pump 16 and newly extracted blood from the patient are supplied by flow control valve 13 to air separator 15 simultaneously. Thus, if the introduction of emboli is related to a low level of blood in air separator 15, additional volumes of blood from the patient can be added while the existing blood flow having the emboli continues to recirculate through air separator 15 until safe, emboli-free blood is detected by sensor 22 and the system can then be restored to the normal operating mode with the valve moving from the recirculate position to the open position.

Figure 4:
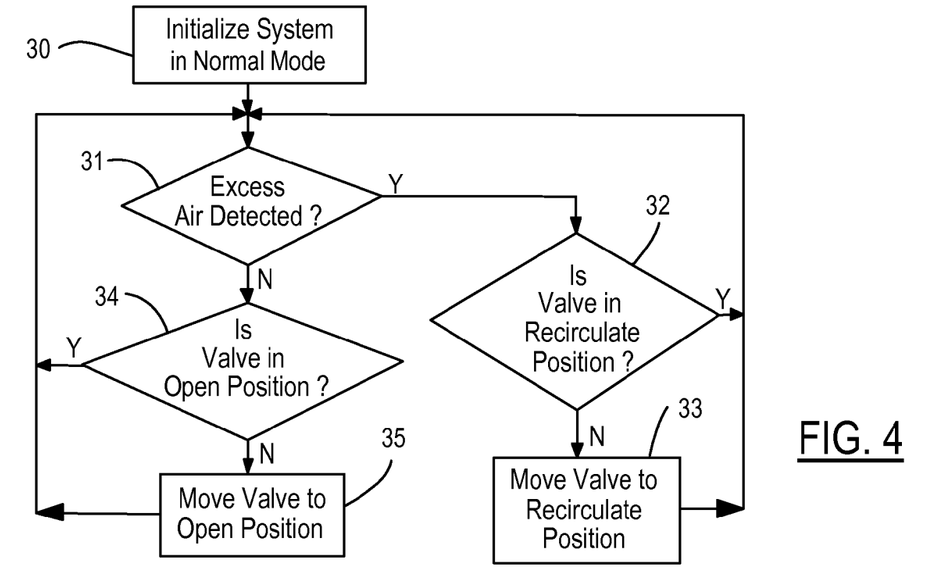
FIG. 4 is a flowchart showing a preferred method for controlling the flow control valve of FIG. 1.

A preferred method for operating the perfusion system is shown in FIG. 4. In step 30, the perfusion system is initialized in the normal mode with the flow control valve in the open position (e.g., after system priming as is known in the art). A check is made in step 31 to determine whether excess air emboli are detected. If they are, then a check is made in step 32 to determine whether the valve is already in the recirculate position. If it is, then a return is made to step 31 for continuously checking the presence of excess air emboli. If the valve is not already in the recirculate position, then the valve is moved to the recirculate position in step 33 and a return is made to step 31.

In step 31, if excess air emboli are not detected then a check is performed step 34 to determine whether the flow control valve is already in the open position. If it is, then a return is made to step 31. Otherwise, the flow control valve is moved to the open position in step 35 and then a return is made to step 31.

In the preferred embodiment, the flow control valve for diverting emboli-containing blood starts out in the normal or open position when operation of the perfusion system is initiated. When emboli or any excess air is detected by a sensor in the blood flow path, the controller or computer moves the flow control valve to the recirculate position so that suspect blood is sent back to the air removal system. Once the air embolism event passes, the flow control valve is returned to the open position thereby permitting blood to be sent to the oxygenator and then the patient. Preferably, the control of the valve is performed electronically by the controller. However, the perfusionist may choose to bypass the controller and activate the valve manually. In particular, the perfusionist may wish to restore the normal circulation mode only after they can verify that the problem leading to the presence of emboli has been corrected. Various types of flow control valve constructions will now be described which can be adapted to both automatic and manual control.

Figure 5:
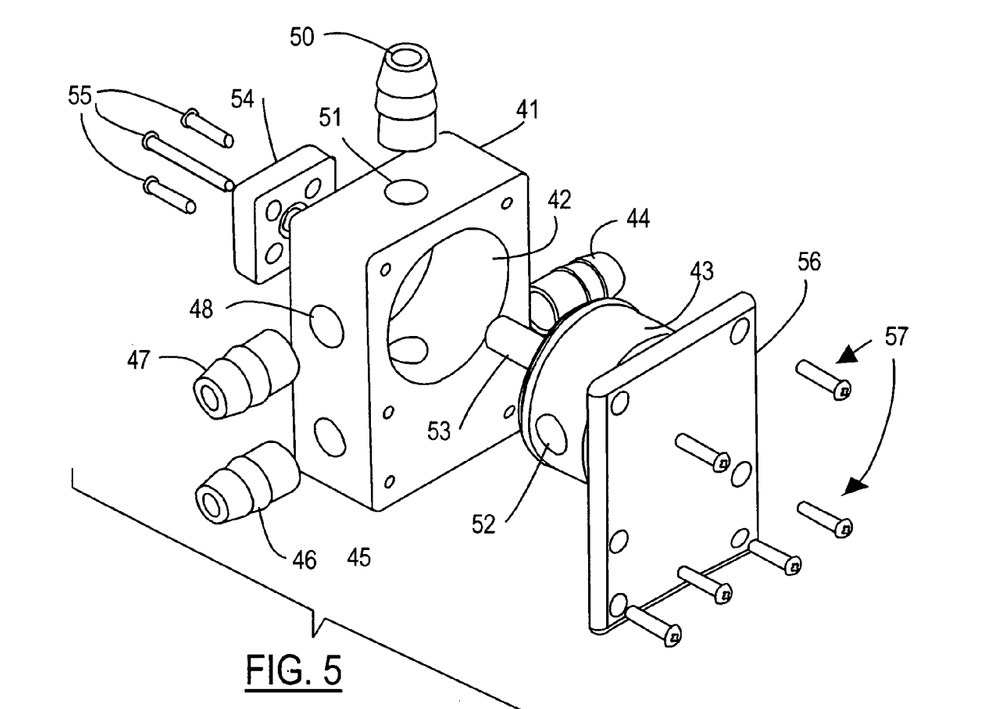
FIG. 5 is an exploded view of a plug valve used in one embodiment of the present invention.

FIG. 5 shows a rotating plug valve 40 including a main body 41 having a cylindrical chamber 42 for receiving a disk-shaped valve element 43. A first inlet is formed by a nozzle 44 joined to a passageway 45 that extends through body 41 to a nozzle 46 for providing the first outlet port. A second inlet port comprises nozzle 47 mounted in communication with a passage 48 leading to chamber 42. A second outlet port comprises a nozzle 50 joined to a passage 51 likewise leading to chamber 42. Passage 45 also communicates with chamber 42. Valve element 43 is received in chamber 42 and has an internal passage 52 for selectively coupling the second inlet nozzle 47 with either second outlet nozzle 50 or first outlet nozzle 46 when element 43 is rotated within cylindrical chamber 42.

Valve element 43 has a control stem 53 extending out through a mating aperture in main body 41 to an actuator 54 which is mounted to the side of main body 41 by a plurality of screws 55. Actuator 54 preferably includes an electrically controlled motor (such as a DC stepper motor) for selectably controlling the rotational position of valve element 43 in response to control signals from the controller. Valve stem 53 and actuator 54 are sealed in order to retain blood within plug valve 40. Likewise, valve element 43 is sealed within cylindrical chamber 42 by a bottom cover 56 mounted to main body 41 using a plurality of screws 57. Main body 41, the nozzles, and cover 56 are preferably comprised of a clear, biocompatible plastic so that blood within the valve can be seen during perfusion.

Figure 6:
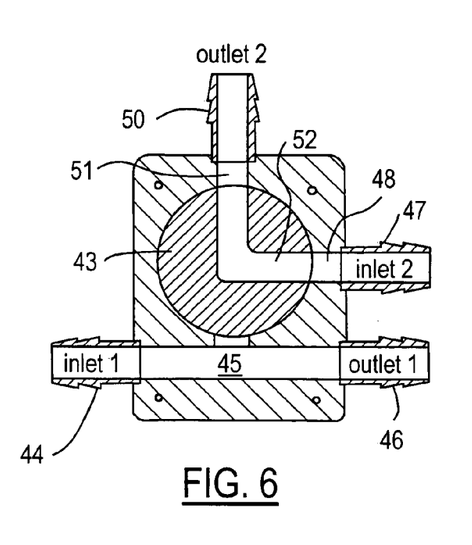
FIG. 6 is a cross-sectional view of the plug valve in its open position.
Figure 7:
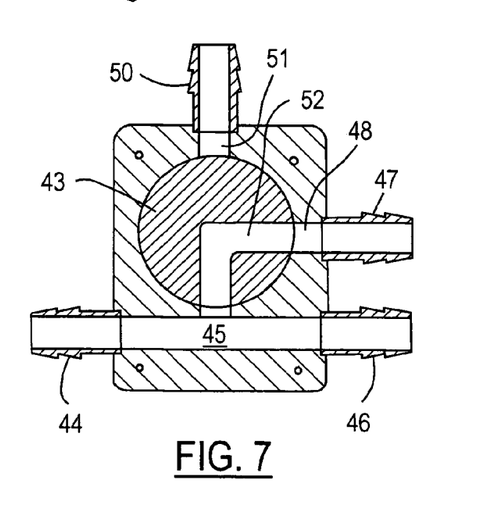
FIG. 7 is a cross-sectional view of the plug valve in its recirculate position.

FIG. 6 illustrates a cross sectional view with valve element 43 rotated to the open position with blood flow proceeding from the first inlet to the first outlet and from the second inlet to the second outlet. FIG. 7 is a cross sectional view with valve element 43 rotated to the recirculate position wherein blood flows from the first inlet to the first outlet and from the second inlet to the first outlet so that emboli-containing blood returns to the air removal system. Simultaneously, fresh blood from the patient can enter the system while the outlet to the oxygenator is isolated so that no flow occurs to the patient.

Figures 8, 9:
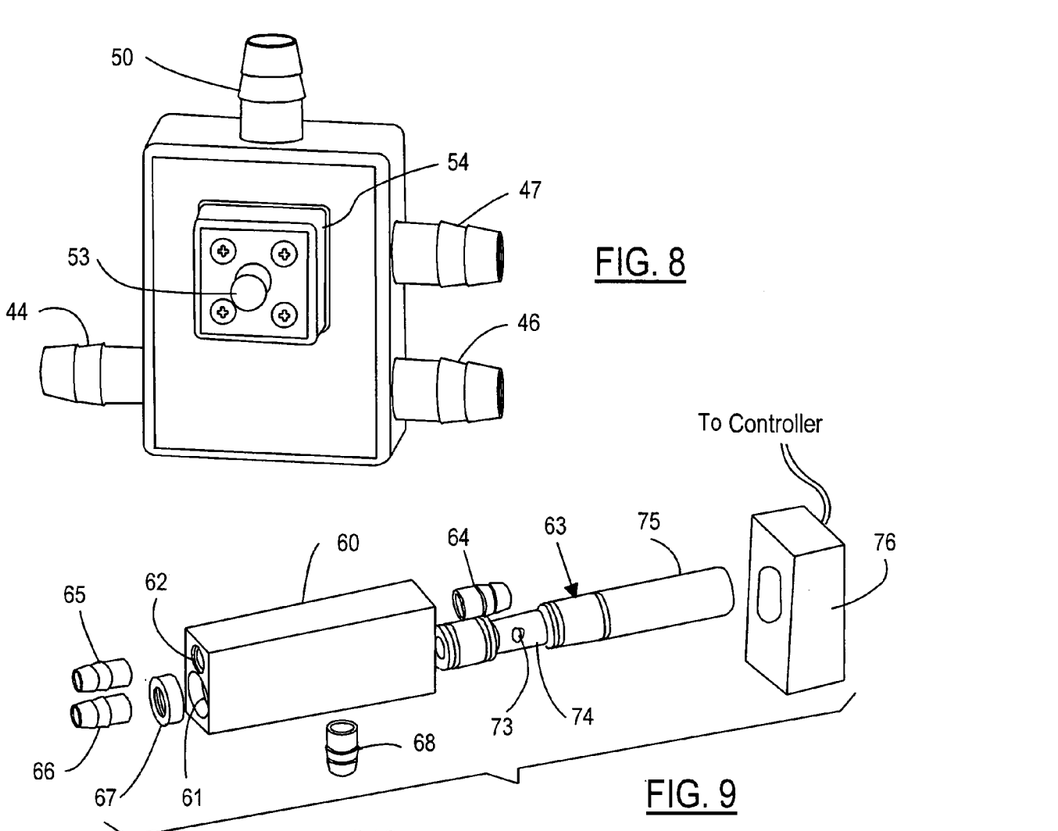
FIG. 8 is an isometric view of the plug valve showing the extension of the valve stem.
FIG. 9 is an exploded view of a piston valve used in another embodiment of the invention.

FIG. 8 shows the actuator side of plug valve 40 with control stem 53 extending through actuator 54. If manual control is desired, a handle can be attached to control stem 53 and the handle and/or valve body labeled to indicate the proper movement of the handle to obtain the open and recirculate positions, respectively.

Figure 10:
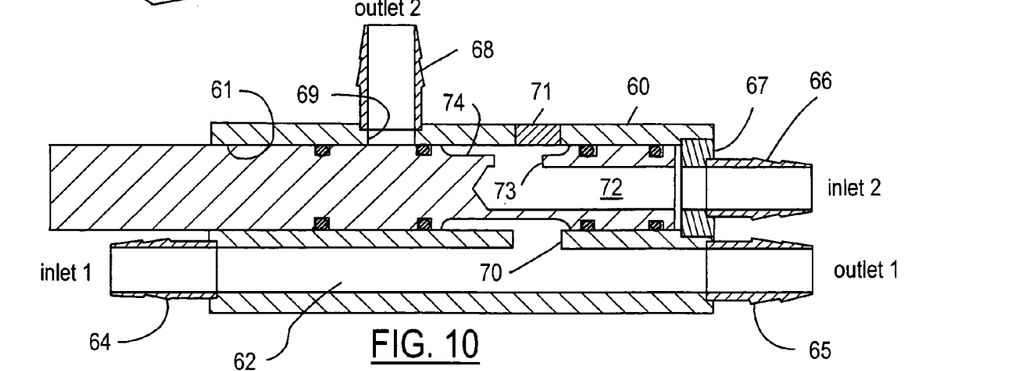
FIG. 10 is a cross-sectional view of the piston valve of FIG. 9.

FIG. 9 shows an exploded view of an alternative embodiment for the control valve wherein a piston-type valve is employed. A main valve body 60 has longitudinal bores 61 and 62 extending therethrough. A movable valve element 63 is received in bore 61. A nozzle 64 is attached to body 61 at one end of bore 62 to form a first inlet as shown in FIG. 10. A nozzle 65 is connected with the other end of bore 62 to provide a first outlet which is coaxial with first inlet nozzle 64. A nozzle 66 is connected to valve body 60 at one end of bore 61 via a connection ring 67 to form a second inlet. A nozzle 68 is connected to an aperture 69 in main body 60 to provide a second outlet. A passageway 70 is provided between bores 61 and 62. It may be formed by drilling through main body 60 and then plugging the exterior hole as shown at 71.

Valve element 63 has an internal passageway 72 that connects one end of valve element 63 to an intermediate exit hole 73 and to a flow recess 74 around the circumference of the valve element. Thus, depending upon the longitudinal position of valve element 63, flow from second inlet 66 is recirculated to first outlet 65 through hole 70 as shown in FIG. 10 or is directed through second outlet 68 when passage 73 and recess 74 are extended to a position aligned with second outlet 68. In order to control the position of valve element 63, a control end 75 is coupled to an actuator 76. Actuator 76 may include a magnetic solenoid, for example.

Figures 11, 12, 13:
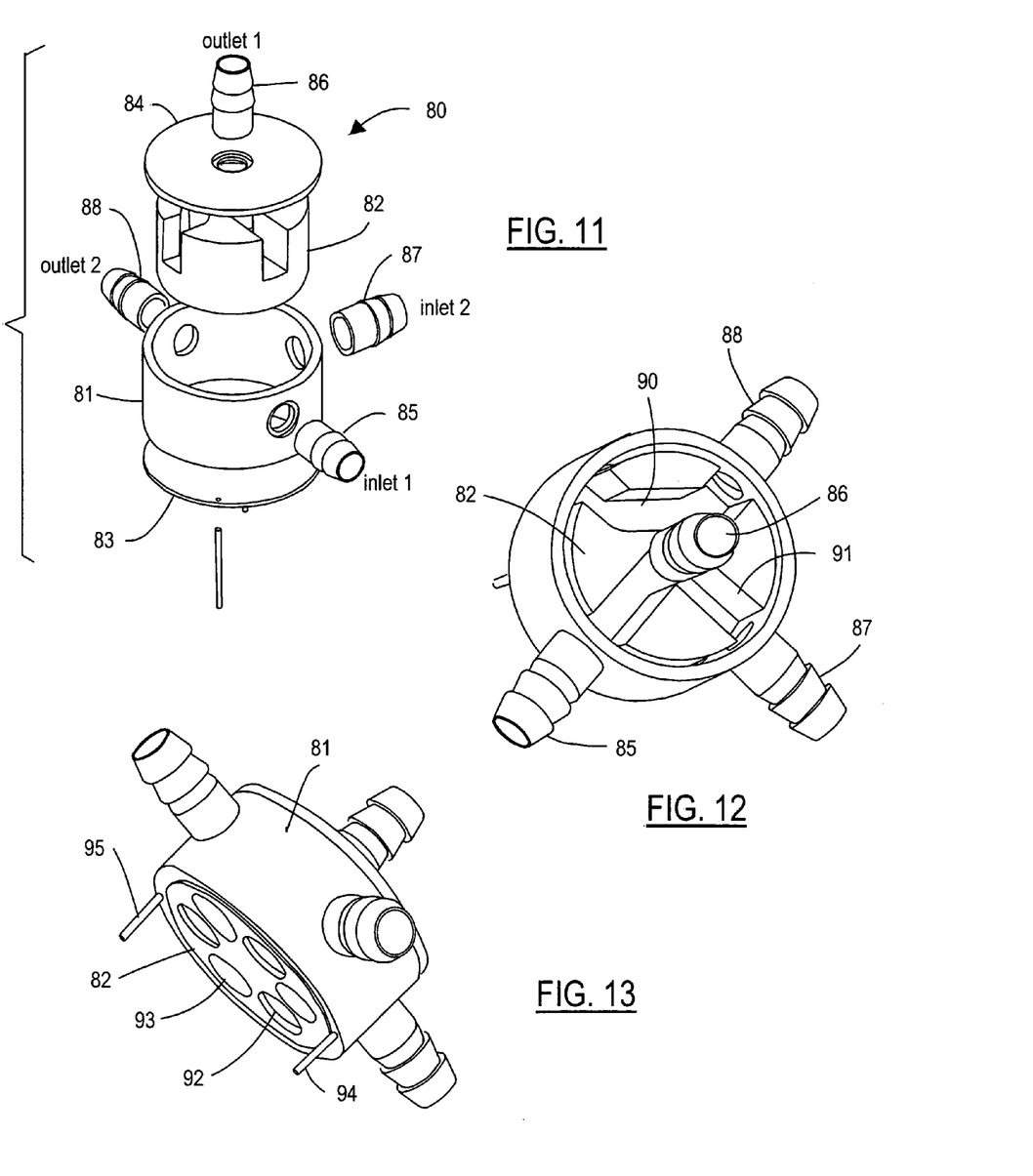
FIG. 11 is an exploded view of an alternate embodiment of a plug valve having magnetic coupling.
FIG. 12 is a perspective view of the plug valve of FIG. 11 with the top cover removed.
FIG. 13 is a perspective view of the bottom of the plug valve of FIG. 11 with the bottom cover removed.

As shown in FIG. 11, an alternate embodiment employing a plug-type valve includes an outer housing wall 81 for receiving a valve element 82. Sealed bottom and top covers 83 and 84 retain valve element 82 in housing 81. A nozzle 85 provides a first inlet port through housing 81 and a nozzle 86 provides a first outlet port through top cover 84. A nozzle 87 provides a second inlet port through housing 81 and a nozzle 88 provides a second outlet port through housing 81.

As shown in FIG. 12, valve element 82 includes a channel 90 and a channel 91 for interconnecting the various ports to provide the open and recirculate positions of the valve. FIG. 12 is shown with cover 84 removed so that channels 90 and 91 can be seen. Valve element 82 is in the recirculate position wherein channel 90 is aligned with second outlet nozzle 88 at one end and is blocked at its opposite end and wherein channel 91 interconnects first inlet nozzle 85 with first outlet nozzle 86 and second inlet nozzle 87. By rotating element 82 clockwise by 90°, the first inlet and outlet ports are interconnected and the second inlet and outlet ports are interconnected, thereby configuring the valve in the open position.

Figure 14:
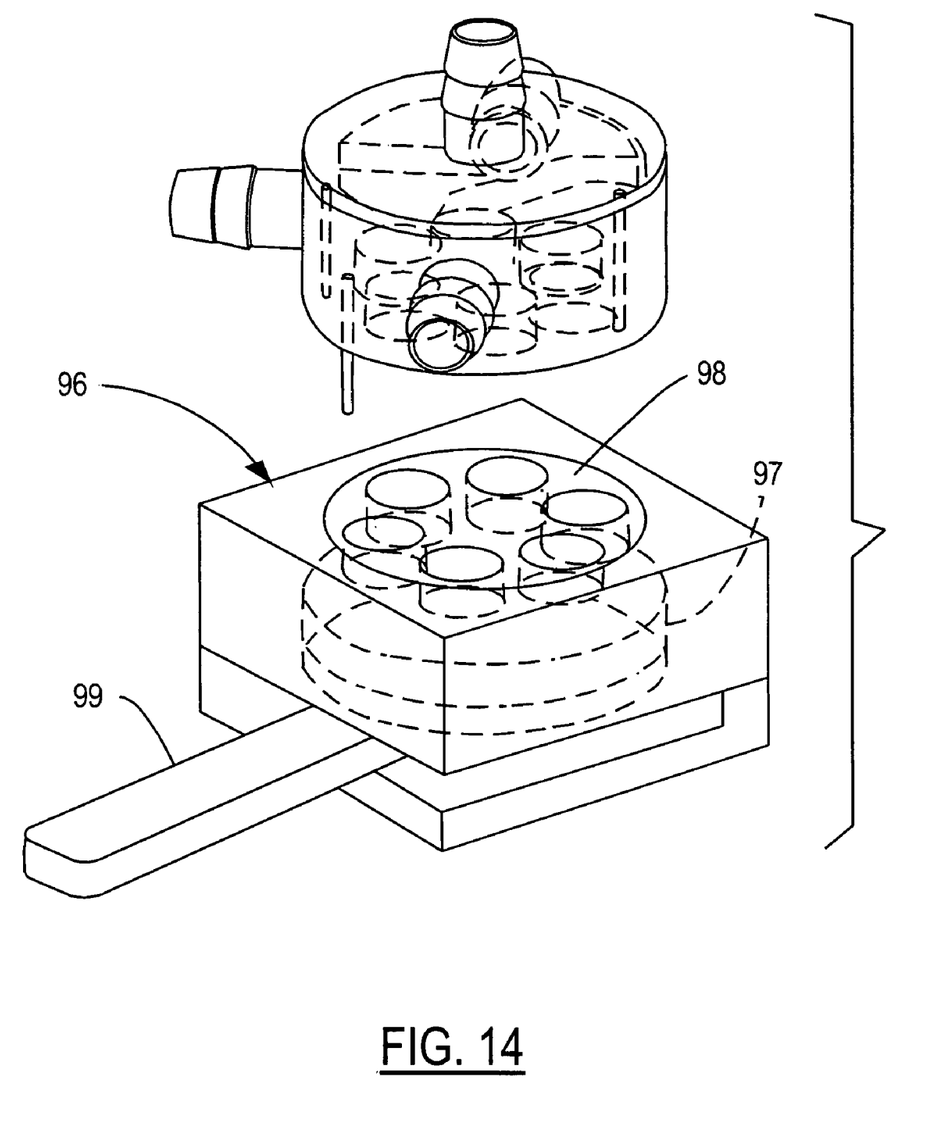
FIG. 14 is a perspective view of the plug valve and a combined automatic/manual actuator.

FIG. 13 shows that a bottom surface of valve element 82 includes a plurality of disk shaped recesses 92 for receiving disk-shaped magnets 93 for providing a magnetic coupling to valve element 82. Pins 94 and 95 extend from housing 81 in order to receive the bottom cover and to facilitate mounting of the valve to an actuator 96 as shown in FIG. 14. A motor 97 is controlled by the controller and drives a magnet disk 98 configured to have magnetic poles for magnetically linking with the magnetic disks 93 on the valve element so that rotation of the valve element matches the rotation of motor 97. A handle 99 is coupled to disk 98 via motor 97 for manually adjusting the position of the valve element.

Figure 15:
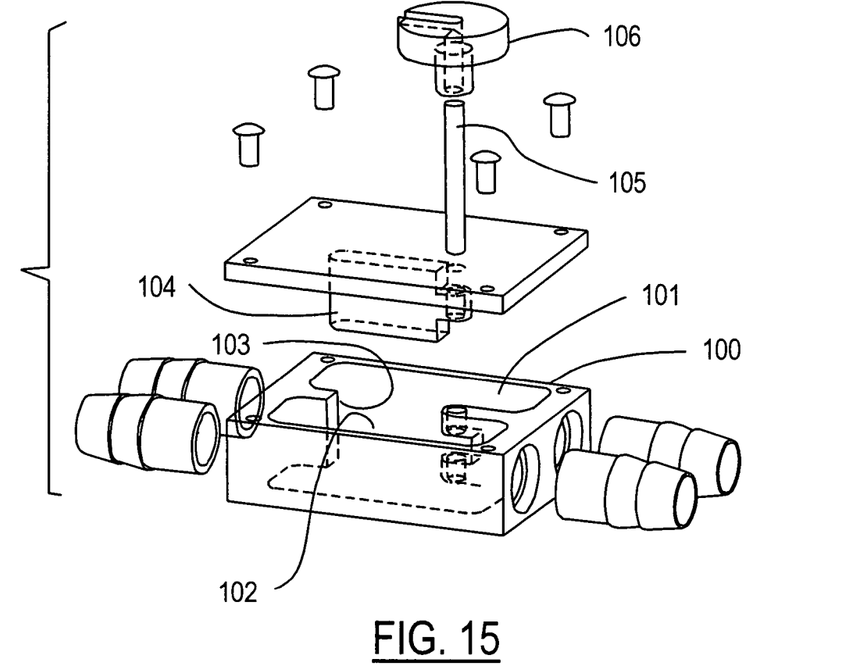
FIG. 15 is an exploded view of a gate valve used in another embodiment of the invention adapted for automatic actuation.
Figure 16:
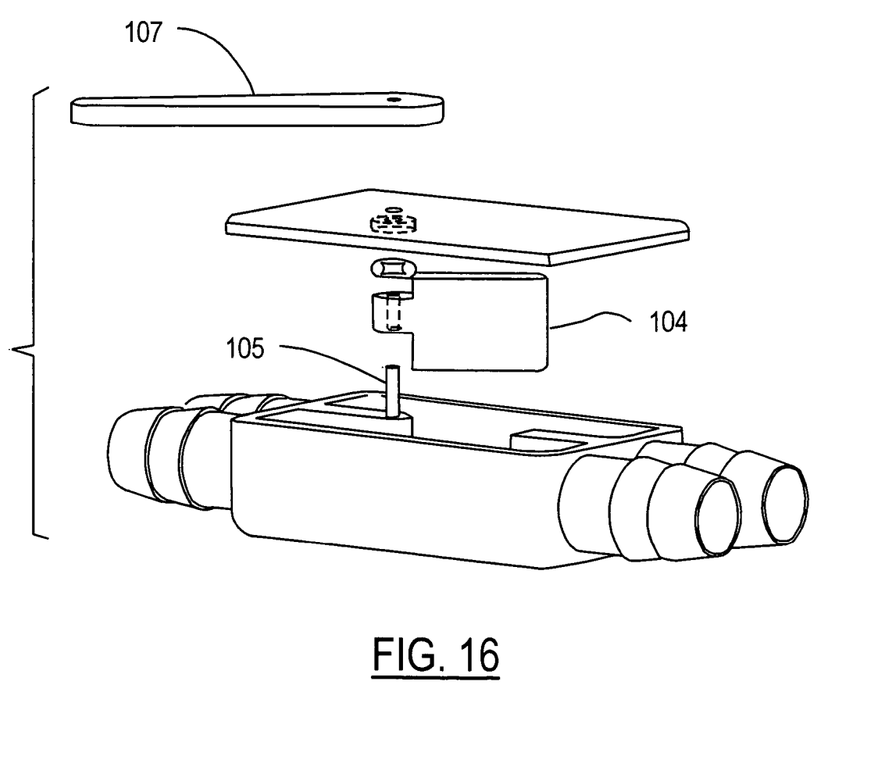
FIG. 16 is an exploded view of a gate valve used in another embodiment of the invention adapted for manual actuation.
Figure 17:
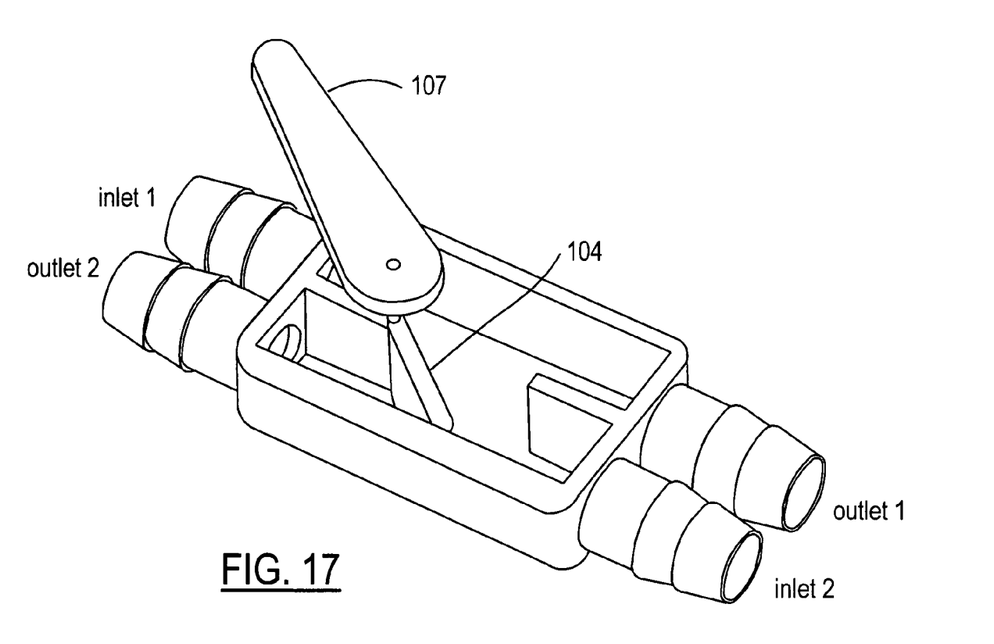
FIG. 17 is a perspective view of the gate valve of FIG. 16 with the top cover removed.
Figure 18:
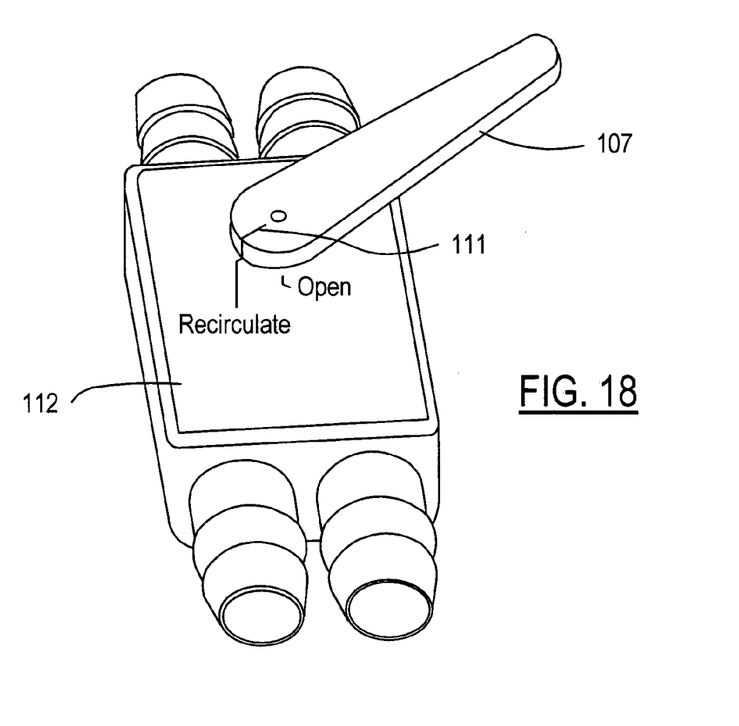
FIG. 18 is a top, perspective view of the gate valve of FIG. 16.

FIGS. 15-18 illustrate the use of a gate-type valve for the flow control valve of the present invention. As shown in FIG. 15, a valve body 100 has parallel flow channels 101 and 102 separated by an opening 103. A rotatable gate 104 is received in opening 103 and may be oriented parallel to the flow channels in order to separate the flow channels and provide the open position of the valve wherein the inlet ports are connected just to their respective output ports. A shaft 105 is connected to gate 104 and has a control wheel 106 adapted to be coupled with an actuator in order to provide an automatically controlled version of the valve. As shown in FIG. 16, a manual version utilizes a handle 107 coupled with shaft 105 for controlling gate 104. FIG. 17 shows handle 107 and gate 104 in a recirculate position so that both inlet ports are coupled to the first outlet port and the second outlet port is isolated. As shown in FIG. 18, handle 107 may include a pointer 111 for aligning with labeling on a cover 112 to show when the valve is in the open or recirculate position.

What is claimed is:

1. A perfusion system for treating blood of a patient during a surgical procedure, comprising:
    a venous line for carrying blood removed from the patient;
    a flow control valve having first and second inlets and first and second outlets, wherein the first inlet is coupled to the venous line;
    an air removal system for removing emboli from the blood flowing in the perfusion system;
    a first intermediate line coupling the first outlet of the flow control valve to the air removal system;
    a second intermediate line coupled to the second inlet of the flow control valve;
    a blood pump coupled to the second intermediate line and the air removal system for pumping the blood from the air removal system to the second inlet of the flow control valve;
    an arterial line coupled to the second outlet of the flow control valve for carrying treated blood back to the patient;
    wherein the flow control valve is selectably placed in an open position or a recirculate position, wherein the first inlet is coupled to the first outlet when the flow control valve is in either the open position or the recirculate position so that blood is substantially continuously removed from the patient, wherein the second inlet is coupled to the second outlet and blocked from the first outlet when the flow control valve is in the open position so that the treated blood is carried back to the patient, and wherein the second inlet is coupled to the first outlet and blocked from the second outlet when the flow control valve is in the recirculate position so that the treated blood is returned to the air removal system and is substantially blocked from returning to the patient.

2. The perfusion system of claim 1 further comprising:
    an actuator for selectably moving the flow control valve between the open and recirculate positions;
    an emboli sensor monitoring performance of the air removal system; and a controller determining whether the emboli sensor detects air in excess of a predetermined threshold and causing the actuator to position the flow control valve in the recirculate position in response to detection of an excess.

3. The perfusion system of claim 2 wherein the emboli sensor is comprised of an air sensor coupled the second intermediate line.

4. The perfusion system of claim 2 wherein the emboli sensor is comprised of a level sensor for monitoring the level of blood present within the air removal system.

5. The perfusion system of claim 2 wherein the flow control valve is manually moveable between the open and recirculate positions.

6. The perfusion system of claim 1 wherein the flow control valve is comprised of a plug valve.

7. The perfusion system of claim 1 wherein the flow control valve is comprised of a piston valve.

8. The perfusion system of claim 1 wherein the flow control valve is comprised of a gate valve.

9. The perfusion system of claim 1 further comprising an annunciator coupled to the controller for generating an alert signal when the controller determines that the emboli sensor is detecting air in excess of a predetermined threshold.

* * * * *